(12) United States Patent
Zhu (10) Patent No.: US 11,504,526 B2
(45) Date of Patent: Nov. 22, 2022

(54) METHODS AND SYSTEMS FOR DISCRETE MEASUREMENT OF ELECTRICAL CHARACTERISTICS (71) Applicant: Boston Scientific Neuromodulation Corporation, Valencia, CA (US)

(72) Inventor: Changfang Zhu, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 16/883,445

(22) Filed: May 26, 2020

(65) Prior Publication Data

US 2020/0376263 A1 Dec. 3, 2020

Related U.S. Application Data (60) Provisional application No. 62/854,514, filed on May 30, 2019.

(51) Int. Cl.
*A61N 1/05* (2006.01)
*A61N 1/36* (2006.01)
*A61N 1/372* (2006.01)

(52) U.S. Cl.
CPC ......... *A61N 1/0553* (2013.01); *A61N 1/0502* (2013.01); *A61N 1/0534* (2013.01);
(Continued)

(58) Field of Classification Search
CPC .. A61N 1/0502; A61N 1/0534; A61N 1/0553; A61N 1/0556; A61N 1/36071;
(Continued)

(56) References Cited

U.S. PATENT DOCUMENTS 5,697,958 A 12/1997 Paul et al.
5,702,429 A 12/1997 King
(Continued)

FOREIGN PATENT DOCUMENTS

WO 2006/119131 11/2006
WO 2012/155186 11/2012
(Continued)

OTHER PUBLICATIONS

International Search Report and Written Opinion for PCT Application No. PCT/US2020/034558 dated Sep. 16, 2020.

*Primary Examiner* — Carl H Layno
*Assistant Examiner* — Anh-Khoa N Dinh
(74) *Attorney, Agent, or Firm* — Branch Partners PLLC; Bruce E. Black (57) ABSTRACT

An electrical stimulation system includes at least one electrical stimulation lead, each of the at least one electrical stimulation lead including a plurality of stimulation electrodes; and a processor coupled to the lead and configured to perform actions, including: directing delivery of at least one electrical pulse through at least one of the stimulation electrodes of the at least one electrical stimulation lead to tissue of a patient; and directing discrete or intermittent measurement of an electrical characteristic of the tissue using at least one of the stimulation electrodes of the at least one electrical stimulation lead during, and after, delivery of the at least one electrical pulse to the tissue of the patient.

20 Claims, 8 Drawing Sheets

(52) U.S. Cl.
CPC ....... *A61N 1/0556* (2013.01); *A61N 1/36071* (2013.01); *A61N 1/37211* (2013.01)

(58) Field of Classification Search
CPC ............ A61N 1/37211; A61N 1/36021; A61N 1/36025; A61N 1/36031; A61N 1/36034; A61N 1/36062; A61N 1/36067; A61N 1/36128; A61N 1/36135; A61N 1/36139; A61N 1/3615; A61N 1/37205; A61N 1/0558; A61N 1/3603; A61N 1/37217; A61B 2018/00642; A61B 2018/00648; A61B 2018/00755; A61B 2018/00839; A61B 2018/00875; A61B 5/407; A61B 5/377; A61B 5/01; A61B 5/0536; A61B 5/291

See application file for complete search history.

(56) References Cited

U.S. PATENT DOCUMENTS

| | | | |
|---|---|---|---|
| 5,902,236 A | 5/1999 | Iverson | |
| 5,902,249 A | 5/1999 | Lyster | |
| 5,913,882 A | 6/1999 | King | |
| 6,181,969 B1 | 1/2001 | Gord | |
| 6,516,227 B1 | 2/2003 | Meadows et al. | |
| 6,560,490 B2 | 5/2003 | Grill et al. | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 7,024,247 B2 | 4/2006 | Gliner et al. | |
| 7,244,150 B1 | 7/2007 | Brase et al. | |
| 7,424,322 B2 | 9/2008 | Lombardi et al. | |
| 7,437,193 B2 | 10/2008 | Parramon et al. | |
| 7,450,992 B1 | 11/2008 | Cameron | |
| 7,450,997 B1 | 11/2008 | Pianca et al. | |
| 7,672,734 B2 | 3/2010 | Anderson et al. | |
| 7,761,165 B1 | 7/2010 | He et al. | |
| 7,783,359 B2 | 8/2010 | Meadows | |
| 7,792,590 B1 | 9/2010 | Pianca et al. | |
| 7,809,446 B2 | 10/2010 | Meadows | |
| 7,949,395 B2 | 5/2011 | Kuzma | |
| 7,974,706 B2 | 7/2011 | Moffitt et al. | |
| 8,175,710 B2 | 5/2012 | He | |
| 8,224,450 B2 | 7/2012 | Brase | |
| 8,255,057 B2 | 8/2012 | Fang et al. | |
| 8,271,094 B1 | 9/2012 | Moffitt et al. | |
| 8,295,944 B2 | 10/2012 | Howard et al. | |
| 8,335,664 B2 | 12/2012 | Eberle | |
| 8,352,030 B2 | 1/2013 | Denison | |
| 8,364,278 B2 | 1/2013 | Pianca et al. | |
| 8,391,985 B2 | 3/2013 | McDonald | |
| 8,606,362 B2 | 12/2013 | He et al. | |
| 8,620,436 B2 | 12/2013 | Parramon et al. | |
| 8,688,235 B1 | 4/2014 | Pianca et al. | |
| 8,768,453 B2 | 7/2014 | Parramon et al. | |
| 9,044,155 B2 | 6/2015 | Strahl | |
| 9,061,140 B2 | 6/2015 | Shi et al. | |
| 9,119,964 B2 | 9/2015 | Marnfeldt | |
| 9,155,892 B2 | 10/2015 | Parker et al. | |
| 9,248,274 B2 | 2/2016 | Troosters et al. | |
| 9,248,279 B2 | 2/2016 | Chen et al. | |
| 9,265,431 B2 | 2/2016 | Hincapie Ordonez et al. | |
| 9,302,112 B2 | 4/2016 | Bornzin et al. | |
| 9,381,356 B2 | 7/2016 | Parker et al. | |
| 9,386,934 B2 | 7/2016 | Parker et al. | |
| 9,399,132 B2 | 7/2016 | Parramon et al. | |
| 9,403,013 B2 | 8/2016 | Walker et al. | |
| 9,409,020 B2 | 8/2016 | Parker | |
| 9,526,897 B2 | 12/2016 | Chen et al. | |
| 9,533,148 B2 | 1/2017 | Carcier | |
| 9,731,116 B2 | 8/2017 | Chen | |
| 9,872,990 B2 | 1/2018 | Parker et al. | |
| 9,974,455 B2 | 5/2018 | Parker et al. | |
| 10,076,667 B2 | 9/2018 | Kaula et al. | |
| 2002/0156513 A1 | 10/2002 | Borkan | |
| 2003/0139781 A1* | 7/2003 | Bradley | A61N 1/0551 607/48 |
| 2005/0246004 A1 | 11/2005 | Cameron et al. | |
| 2007/0150036 A1 | 6/2007 | Anderson | |
| 2008/0146894 A1 | 6/2008 | Bulkes et al. | |
| 2009/0187222 A1 | 7/2009 | Barker | |
| 2009/0276021 A1 | 11/2009 | Meadows et al. | |
| 2010/0030286 A1* | 2/2010 | Goetz | A61N 1/37 607/2 |
| 2010/0076535 A1 | 3/2010 | Pianca et al. | |
| 2010/0268298 A1 | 10/2010 | Moffitt et al. | |
| 2010/0331916 A1 | 12/2010 | Parramon et al. | |
| 2011/0004267 A1 | 1/2011 | Meadows | |
| 2011/0005069 A1 | 1/2011 | Pianca | |
| 2011/0078900 A1 | 4/2011 | Pianca et al. | |
| 2011/0106215 A1* | 5/2011 | Moffitt | A61N 1/37247 607/60 |
| 2011/0130817 A1 | 6/2011 | Chen | |
| 2011/0130818 A1 | 6/2011 | Chen | |
| 2011/0238129 A1 | 9/2011 | Moffitt et al. | |
| 2011/0313500 A1 | 12/2011 | Barker et al. | |
| 2012/0016378 A1 | 1/2012 | Pianca et al. | |
| 2012/0046710 A1 | 2/2012 | DiGiore et al. | |
| 2012/0071949 A1 | 3/2012 | Pianca et al. | |
| 2012/0092031 A1 | 4/2012 | Shi et al. | |
| 2012/0095519 A1 | 4/2012 | Parramon et al. | |
| 2012/0095529 A1 | 4/2012 | Parramon et al. | |
| 2012/0165911 A1 | 6/2012 | Pianca | |
| 2012/0197375 A1 | 8/2012 | Pianca et al. | |
| 2012/0203316 A1 | 8/2012 | Moffitt et al. | |
| 2012/0203320 A1 | 8/2012 | DiGiore et al. | |
| 2012/0203321 A1 | 8/2012 | Moffitt et al. | |
| 2012/0316615 A1 | 12/2012 | DiGiore et al. | |
| 2013/0105071 A1 | 5/2013 | DiGiore et al. | |
| 2013/0197602 A1 | 8/2013 | Pianca et al. | |
| 2013/0289665 A1 | 10/2013 | Marnfeldt et al. | |
| 2014/0031901 A1 | 1/2014 | Zhu et al. | |
| 2014/0194772 A1 | 7/2014 | Single et al. | |
| 2014/0236042 A1 | 8/2014 | Parker et al. | |
| 2014/0296737 A1 | 10/2014 | Parker et al. | |
| 2015/0018699 A1 | 1/2015 | Zeng et al. | |
| 2015/0119751 A1 | 4/2015 | Stanslaski et al. | |
| 2015/0157861 A1 | 6/2015 | Aghassian | |
| 2015/0282725 A1 | 10/2015 | Single | |
| 2015/0313487 A1 | 11/2015 | Single et al. | |
| 2015/0360038 A1 | 12/2015 | Zottola et al. | |
| 2016/0051812 A1* | 2/2016 | Montgomery, Jr. | A61N 1/0534 600/546 |
| 2016/0166164 A1 | 6/2016 | Obradovic et al. | |
| 2016/0287126 A1 | 10/2016 | Parker et al. | |
| 2016/0287182 A1 | 10/2016 | Single | |
| 2017/0049345 A1 | 2/2017 | Single | |
| 2017/0071490 A1 | 3/2017 | Parker et al. | |
| 2017/0135624 A1 | 5/2017 | Parker | |
| 2017/0136243 A1 | 5/2017 | Lee et al. | |
| 2017/0157410 A1 | 6/2017 | Moffitt et al. | |
| 2017/0173335 A1 | 6/2017 | Min et al. | |
| 2017/0216587 A1 | 8/2017 | Parker | |
| 2017/0259065 A1 | 9/2017 | Baru et al. | |
| 2017/0296823 A1 | 10/2017 | Hershey et al. | |
| 2017/0361101 A1 | 12/2017 | Single | |
| 2018/0071513 A1 | 3/2018 | Weiss et al. | |
| 2018/0071520 A1 | 3/2018 | Weerakoon et al. | |
| 2018/0071527 A1 | 3/2018 | Feldman et al. | |
| 2018/0110987 A1 | 4/2018 | Parker | |
| 2018/0117335 A1 | 5/2018 | Parker et al. | |
| 2018/0132747 A1 | 5/2018 | Parker et al. | |
| 2018/0132760 A1 | 5/2018 | Parker | |
| 2018/0133459 A1 | 5/2018 | Parker et al. | |
| 2018/0140831 A1 | 5/2018 | Feldman et al. | |
| 2018/0228391 A1 | 8/2018 | Parker et al. | |
| 2018/0228547 A1 | 8/2018 | Parker et al. | |
| 2018/0256052 A1 | 9/2018 | Parker et al. | |
| 2018/0289967 A1 | 10/2018 | Bokil | |
| 2019/0099602 A1 | 4/2019 | Esteller et al. | |
| 2019/0175915 A1 | 6/2019 | Brill et al. | |
| 2019/0209844 A1 | 7/2019 | Esteller et al. | |

(56) References Cited

U.S. PATENT DOCUMENTS

| | | |
|---|---|---|
| 2019/0275331 A1 | 9/2019 | Zhu |
| 2019/0290900 A1 | 9/2019 | Esteller et al. |
| 2019/0298992 A1 | 10/2019 | Zhang et al. |
| 2019/0299006 A1 | 10/2019 | Marnfeldt |
| 2019/0366094 A1 | 12/2019 | Esteller et al. |
| 2020/0155019 A1 | 5/2020 | Esteller et al. |
| 2020/0305745 A1 | 10/2020 | Wagenbach et al. |

FOREIGN PATENT DOCUMENTS

| | | |
|---|---|---|
| WO | 2015/077362 | 5/2015 |
| WO | 2017/100866 | 6/2017 |
| WO | 2017/173493 | 10/2017 |
| WO | 2017/210352 | 12/2017 |
| WO | 2017/219096 | 12/2017 |

\* cited by examiner

METHODS AND SYSTEMS FOR DISCRETE MEASUREMENT OF ELECTRICAL CHARACTERISTICS

CROSS-REFERENCE TO RELATED APPLICATIONS

This application claims the benefit under 35 U.S.C. § 119(e) of U.S. Provisional Patent Application Ser. No. 62/854,514, filed May 30, 2019, which is incorporated herein by reference.

FIELD

The present disclosure is directed to the area of implantable electrical stimulation systems and methods of making and using the systems. The present disclosure is also directed to methods and systems for making discrete or intermittent measurements of electrical characteristics using implanted electrical stimulation leads.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Deep brain stimulation can be used to treat a variety of diseases and disorders.

Stimulators have been developed to provide therapy for a variety of treatments. A stimulator can include a control module (with a pulse generator) and one or more stimulator electrodes. The one or more stimulator electrodes can be disposed along one or more leads, or along the control module, or both. The stimulator electrodes are in contact with or near the nerves, muscles, or other tissue to be stimulated. The pulse generator in the control module generates electrical pulses that are delivered by the electrodes to body tissue.

BRIEF SUMMARY

One aspect is an electrical stimulation system including at least one electrical stimulation lead, each of the at least one electrical stimulation lead including a plurality of stimulation electrodes; and a processor coupled to the lead and configured to perform actions, including: directing delivery of at least one electrical pulse through at least one of the stimulation electrodes of the at least one electrical stimulation lead to tissue of a patient; and directing discrete measurement of an electrical characteristic of the tissue using at least one of the stimulation electrodes of the at least one electrical stimulation lead during, and after (and, optionally, before), delivery of the at least one electrical pulse to the tissue of the patient. In at least some aspects, the discrete measurements can also be characterized as intermittent measurements.

Another aspect is a non-transitory computer-readable medium having stored thereon instructions for execution by a processor, including directing delivery of at least one electrical pulse through at least one stimulation electrode of at least one electrical stimulation lead to tissue of a patient; and directing discrete measurement of an electrical characteristic of the tissue using at least one stimulation electrode of the at least one electrical stimulation lead during, and after (and, optionally, before), delivery of the at least one electrical pulse to the tissue of the patient. In at least some aspects, the discrete measurements can also be characterized as intermittent measurements.

In at least some aspects, the electrical characteristic is an electric field potential. In at least some aspects, the electrical characteristic is a local current. In at least some aspects, the at least one electrical pulse is a therapeutic stimulation pulse. In at least some aspects, the at least one electrical pulse is not a therapeutic stimulation pulse. In at least some aspects, the at least one electrical pulse has an intensity (for example, amplitude, pulse width, or both) that is at a sub-perception level. In at least some aspects, the at least one electrical pulse has an intensity that is at a supra-perception level. In at least some aspects, the shape of the electrical pulse is rectangular. In at least some aspects, the shape of the electrical pulse is non-rectangular, such as, for example, ramp up, wind down, triangular, sinusoidal, exponential, or the like. In at least some embodiments, directing the discrete measurement includes directing discrete measurement of an electrical characteristic of the tissue using at least one non-stimulation electrode on the at least one electrical stimulation lead or at least one electrode that is not disposed on the at least one electrical stimulation lead.

In at least some aspects, directing delivery includes directing delivery of the at least one electrical pulse through two of the stimulation electrodes. In at least some aspects, the at least one electrical pulse includes at least one first electrical pulse and at least one second electrical pulse, wherein directing delivery includes directing delivery of the at least one first electrical pulse through a first pair of the stimulation electrodes and directing delivery of the at least one second electrical pulse through a second pair of the stimulation electrodes. In at least some aspects, directing discrete measurement comprises directing discrete measurement of the electrical characteristic of the tissue using a first pair of the stimulation electrodes to produce a set of first measurements and directing discrete measurement of the electrical characteristic of the tissue using a second pair of the stimulation electrodes to produce a set of second measurements. In at least some aspects, directing discrete measurement comprises producing the first measurements and second measurements during, and after, both the at least first electrical pulse and the at least one second electrical pulse.

In at least some aspects, directing discrete measurement includes directing discrete measurement of the electrical characteristic of the tissue using two of the stimulation electrodes. In at least some aspects, directing discrete measurement includes directing discrete measurement of the electrical characteristic of the tissue using a first pair of the stimulation electrodes to produce a set of first measurements and directing discrete measurement of the electrical characteristic of the tissue using a second pair of the stimulation electrodes to produce a set of second measurements. In at least some aspects, the actions further include determining a differential measurement by subtracting one of the first measurements from one of the second measurements.

In at least some aspects, the actions further include analyzing the discrete measurements to identify a temporal or spatial variation of the electrical characteristic. In at least some aspects, the actions further include extracting a feature or recognizing a pattern in the discrete measurements or the temporal or spatial variation of the electrical characteristic. In at least some aspects, the actions further include deriving a characterization of the tissue or the patient using the extracted feature, the recognized pattern, or the temporal or spatial variation of the electrical characteristic. In at least some aspects, the actions further include altering a set of stimulation parameters based on the characterization of the tissue or the patient, the extracted feature, the recognized pattern, or the temporal or spatial variation of the electrical characteristic. In at least some aspects, the actions further include calibrating a set of measurements based on the characterization of the tissue or the patient, the extracted feature, the recognized pattern, or the temporal or spatial variation of the electrical characteristic.

In at least some aspects, the at least one electrical pulse the at least one electrical pulse includes at least two phases and directing discrete measurement comprises directing at least one measurement during each of the phases of the at least one electrical pulse. In at least some aspects, directing discrete measurement includes directing discrete measurement to start or end only after occurrence of a triggering event. In at least some aspects, directing discrete measurement includes directing discrete measurement only during scheduled measurement periods with no measurement occurring during scheduled measurement-off periods.

In at least some aspects, directing discrete measurement includes directing discrete measurement at a sampling rate of no more than 20 kHz. In at least some aspects, directing discrete measurement includes directing discrete measurement at a sampling rate of no more than 1 kHz.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present disclosure is directed to the area of implantable electrical stimulation systems and methods of making and using the systems. The present disclosure is also directed to methods and systems for making discrete or intermittent measurements of electrical characteristics using implanted electrical stimulation leads.

Suitable implantable electrical stimulation systems include, but are not limited to, a least one lead with one or more electrodes disposed on a distal portion of the lead and one or more terminals disposed on one or more proximal portions of the lead. Leads include, for example, percutaneous leads, paddle leads, cuff leads, or any other arrangement of electrodes on a lead. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated herein by reference. In the discussion below, a percutaneous lead will be exemplified, but it will be understood that the methods and systems described herein are also applicable to paddle leads and other leads.

A percutaneous lead for electrical stimulation (for example, deep brain, spinal cord, or peripheral nerve stimulation) includes stimulation electrodes that can be ring electrodes, segmented electrodes that extend only partially around the circumference of the lead, or any other type of electrode, or any combination thereof. The segmented electrodes can be provided in sets of electrodes, with each set having electrodes circumferentially distributed about the lead at a particular longitudinal position. A set of segmented electrodes can include any suitable number of electrodes including, for example, two, three, four, or more electrodes. For illustrative purposes, the leads are described herein relative to use for spinal cord stimulation, but it will be understood that any of the leads can be used for applications other than spinal cord stimulation, including deep brain stimulation, peripheral nerve stimulation, dorsal root ganglion stimulation, sacral nerve stimulation, or stimulation of other nerves, muscles, and tissues.

Figure 1:
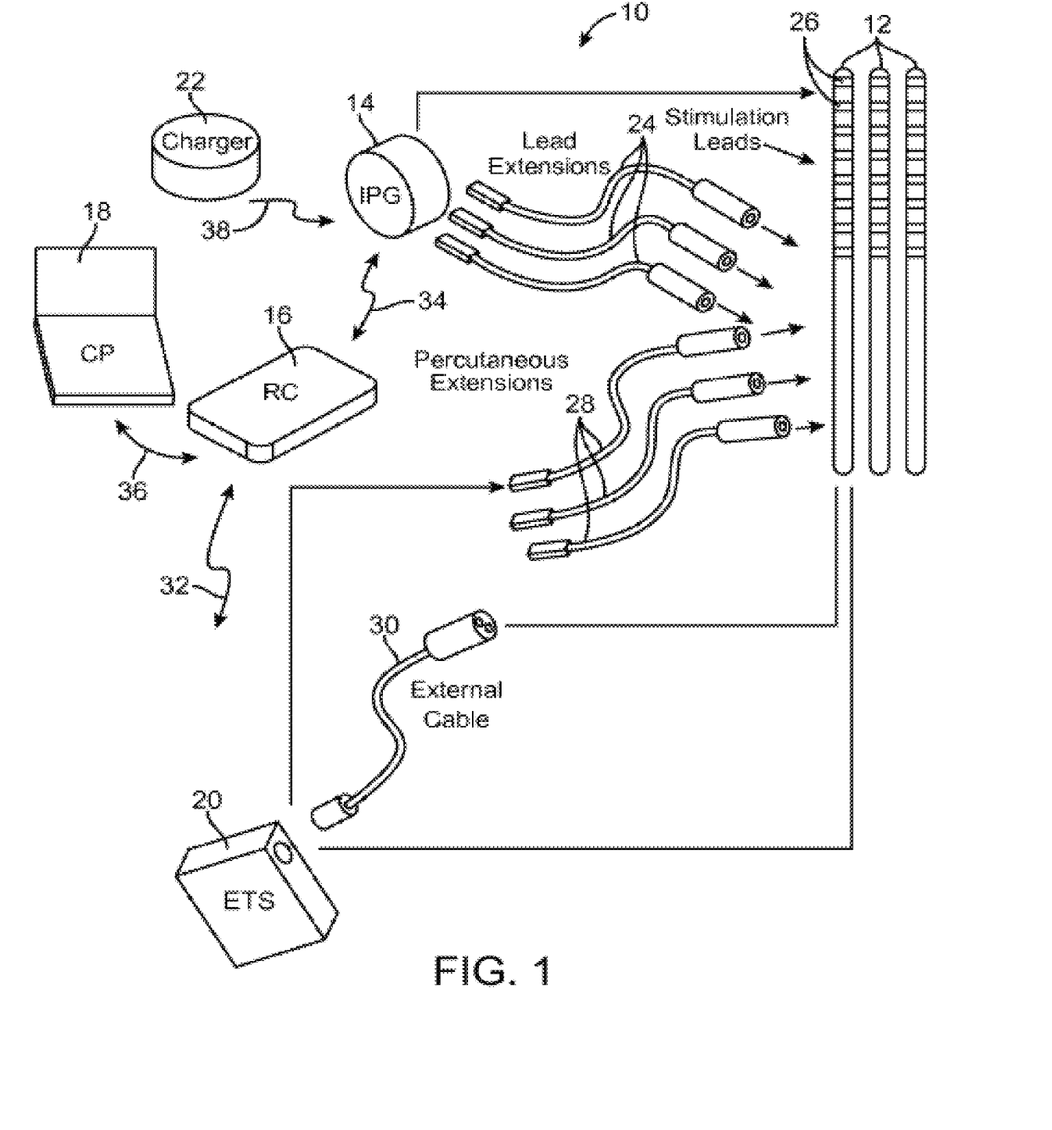
FIG. 1 is a schematic view of one embodiment of an electrical stimulation system.

Turning to FIG. 1, one embodiment of an electrical stimulation system 10 includes one or more stimulation leads 12 and an implantable pulse generator (IPG) 14. The system 10 can also include one or more of an external remote control (RC) 16, a clinician's programmer (CP) 18, an external trial stimulator (ETS) 20, or an external charger 22. The IPG and ETS are examples of control modules for the electrical stimulation system.

The IPG 14 is physically connected, optionally via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The implantable pulse generator can be implanted into a patient's body, for example, below the patient's clavicle area or within the patient's buttocks or abdominal cavity or at any other suitable site. The implantable pulse generator can have multiple stimulation channels which may be independently programmable to control the magnitude of the current stimulus from each channel. In some embodiments, the implantable pulse generator can have any suitable number of stimulation channels including, but not limited to, 4, 6, 8, 12, 16, 32, or more stimulation channels. The implantable pulse generator can have one, two, three, four, or more connector ports, for receiving the terminals of the leads and/or lead extensions.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions. Alternately, or additionally, stimulation parameters can be programed via wireless communications (e.g., Bluetooth) between the RC 16 (or external device such as a hand-held electronic device) and the IPG 14.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18). In at least some embodiments, the CP 18 or RC 16 can be a mobile device, such as a mobile phone.

For purposes of brevity, the details of the RC 16, CP 18, ETS 20, and external charger 22 will not be further described herein. Details of exemplary embodiments of these devices are disclosed in U.S. Pat. No. 6,895,280, which is expressly incorporated herein by reference. Other examples of electrical stimulation systems can be found at U.S. Pat. Nos. 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, as well as the other references cited above, all of which are incorporated herein by reference.

Knowledge and characterization of the local stimulation environment around a lead or the electrodes of a lead can provide useful information. For example, information regarding the impedance, conductivity, or capacitance of the tissue near the lead or electrodes, stimulation induced voltage distribution, current intensity, or charging and discharging characteristics, changes associated with heartbeat and respiration, changes associated with postural position or intensity of physical activities, as well as other electrical characteristics of the tissue, can be determined. Changes in the local stimulation environment may indicate the development, presence, or alterations in scar tissue or fluid around the lead, or electrode, may indicate thickness of fat tissue, thickness of cerebral spinal fluid (for spinal cord stimulation systems), may indicate lead position in the spinal canal, may indicate the relative lead position or electrode position in a multiple lead array, may be used to indicate, infer or determine patient posture or activity, or the like or any combination thereof.

As described herein, electrodes of the lead(s) can be used to sense local electrical characteristics of the environment around the lead(s) and electrodes during and between electrical pulses (which can be, for example, therapeutic stimulation pulses, supra- or sub-perception pulses, dedicated sensing pulses, charge-balancing pulses or other electrical pulses or combinations thereof.) The pulses can have one or more phases and can also include, for example, a pre-pulse, recharge pulse, inter-pulse, or the like. The shape of the electrical pulses can be rectangular or non-rectangular (for example, ramp up, wind down, triangular, sinusoidal, exponential, or the like or any combination thereof) Sensing measurements will be exemplified herein by the measurement of electrical field potentials around the lead(s) and electrodes. It will be understood that other electrical characteristics, such as local currents, resistance, or impedance, can be measured in addition to, or as an alternative to, the electric field potentials and that the description presented herein can be readily applied to these other electrical characteristics (e.g., using constant voltage sources instead of constant current sources.) In at least some embodiments, the electrical pulse has an intensity (for example, amplitude, pulse width, or both) that is sub-perception or supra-perception.

In addition to being dependent on the physical and electrical characteristics of the local tissue, the electric field potential can be affected by a variety of different signals including, but not limited to, stimulation and other electrical pulses, source configuration, measurement configuration, neural response, neural signals, heartbeat signals, respiration, patient activity (e.g., sleep, active, inactive, etc.), posture, and the like. Measurement and observation of the electric field potentials, as described herein, can be used to determine or observe one or more of these signals, as well as information about, and changes in, the local environment as described above.

Figure 2:
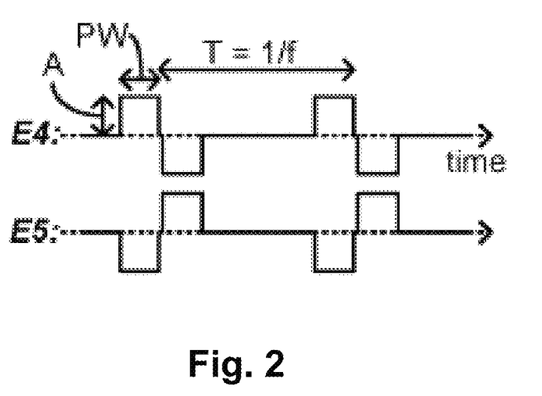
FIG. 2 is a schematic illustration of one embodiment of a biphasic electrical pulse using electrodes E4 and E5.

Measurements may be made before stimulation, during stimulation, and after stimulation pulses to interrogate the local environment. FIG. 2 illustrates an example of stimulation pulses according to a particular stimulation program and as executable by the IPG or ETS 70. In this example, stimulation is provided by electrodes 4 and 5 (E4 and E5) of a lead and each stimulation pulse is biphasic, meaning that a first pulse phase is quickly followed by an opposite polarity second pulse phase. The duration and amplitude of the two phases can be symmetric or asymmetric. The pulse width (PW) can be the duration of either of the pulse phases individually as shown, or can be the entire duration of the biphasic pulse including both pulse phases. The frequency (f) and amplitude (A) of the pulses is also shown in FIG. 2. Although not shown, monophasic pulses—having only a first pulse phase but not followed by an active-charge recovery second pulse phase—can also be used. Other multi-phasic pulse designs for charge balancing can be used.

Biphasic pulses are useful because the second pulse phase can actively recover any charge build up after the first pulse phase residing on capacitances (such as the DC-blocking capacitors in the IPG or ETS) in the current paths between the active electrodes. In the example stimulation program shown in FIG. 2, electrode E4 is selected as the anode electrode while electrode E5 is selected as the cathode electrode (during the first pulse phase). Because two electrodes 16 are used, this represents bipolar stimulation. The pulses as shown are pulses of constant current and the amplitude of the current at any point in time is equal but opposite such that current injected into the patient's tissue by one electrode (e.g., E4) is removed from the tissue by the other electrode (E5). The area of the phases of the first and second pulses are equal, providing active charge recovery of the same amount of charge during each pulse phase. Although not shown, more than two electrodes can be active at any given time to produce multipolar stimulation. For example, electrode E4 could comprise an anode providing a +10 mA current pulse amplitude, while electrodes E3 and E5 could both comprise cathodes with −7 mA and −3 mA current pulse amplitudes respectively. Monopolar stimulation can utilize one electrode on the lead and a second electrode that is distant from the lead, such as the case of the IPG.

Figure 3:
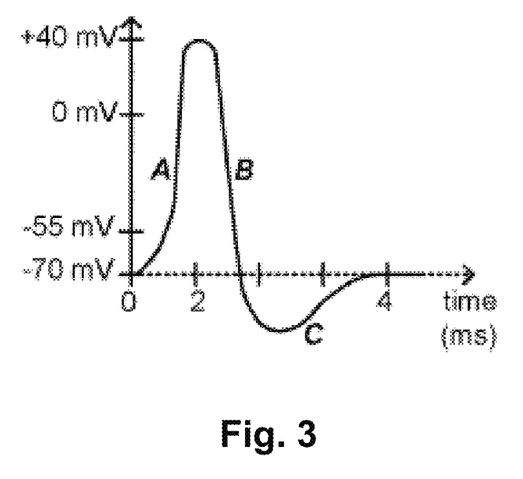
FIG. 3 is a schematic illustration of one embodiment of a neural response or neural signal.

Measurements may be useful for observing or measuring neural response to the electrical pulses or other neural signals such as the transmission of signals to or from the brain along neural pathways. FIG. 3 illustrates one example of a neural response or neural signal. When a neural fiber is recruited by electrical stimulation, it will issue an action potential—that is, the neural fiber will "fire." An action potential for a typical neural fiber is shown in FIG. 3. Should recruitment from electrical stimulation cause the neural fiber's resting state (e.g., −70 mV as measured from inside the cell) to exceed a threshold (e.g., −55 mV), the neural fiber will depolarize ("A"), repolarize ("B"), and hyperpolarize ("C") before coming to rest again. If electrical stimulation continues, the neural fiber will fire again at some later time. Typically, the action potential does not change in magnitude for a given neural fiber. Instead, changing the strength of stimulation may affect the timing at which each action potential is generated, as well as the frequency at which action potentials are issued, and may also affect what types of neural fibers are recruited and the region within which neural fibers are recruited. Each neural fiber is unique in its shape, size, and electrophysical properties, and thus can fire at its own maximum frequency.

Figure 4A:
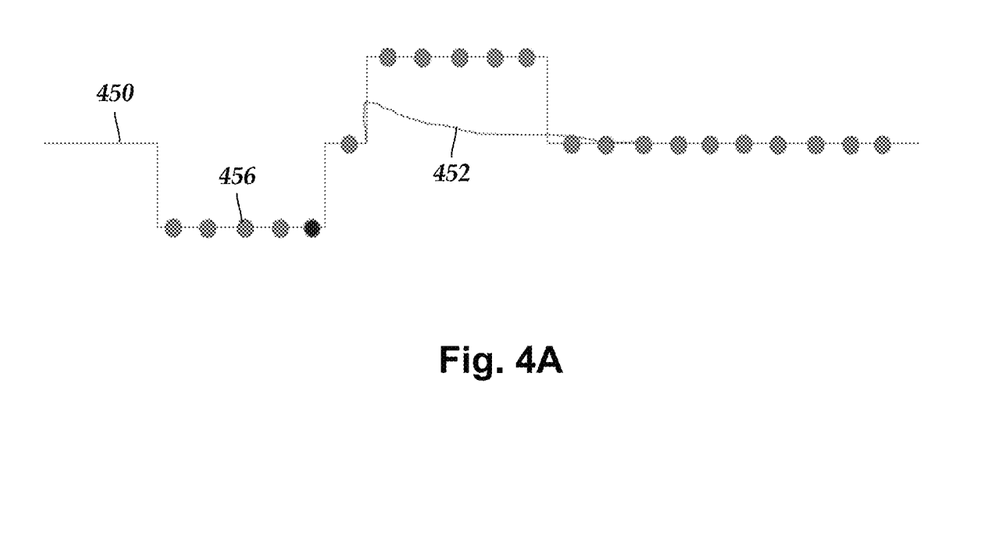
FIG. 4A is a schematic illustration of one embodiment of a graph of voltage versus time for an electrical pulse and neural response with discrete measurements indicated by dots.
Figure 4B:
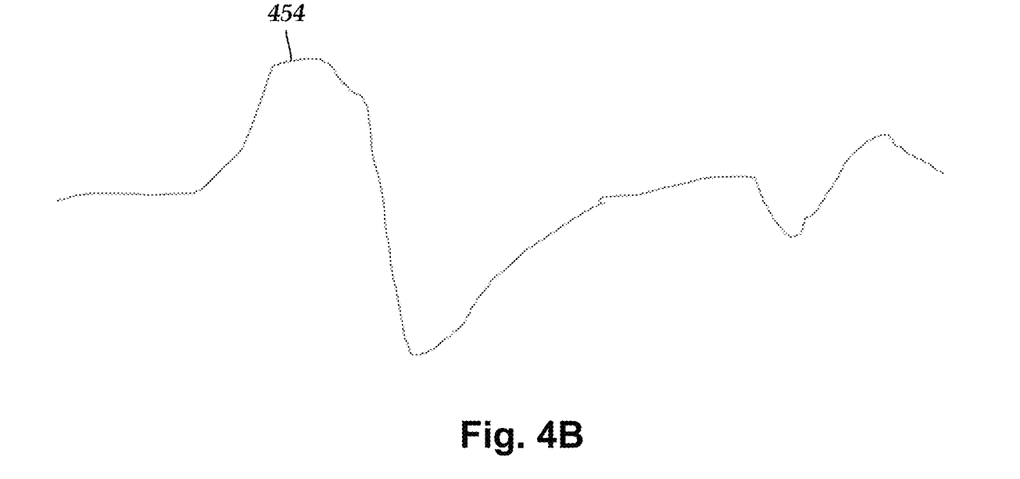
FIG. 4B is a schematic illustration of one embodiment of a graph of voltage versus time of an electric field potential.

In at least some embodiments, the electric field potential can be discretely or intermittently measured during and between electrical pulses, as illustrated in FIGS. 4A and 4B. FIG. 4A is a graph of voltage versus time illustrating one embodiment of an electrical pulse 450 and a representation of a neural response 452. Other electrical activity (which may include neural activity, heartbeat, respiration, posture change, or any other activity that alters the electrical characteristics of the local tissue) may also alter the electric field potential. FIG. 4B illustrates one example of an electric field potential 454 over this period of time accounting for all of the electrical activity include the electrical pulse 450 and local tissue electrical activity 452. The electrical pulse 450 can be used to interrogate the tissue between and near the electrodes utilized to deliver the electrical pulse 450.

The dots 456 in FIG. 4A illustrate one embodiment of discrete, intermittent sensor measurements made using the electrodes of the lead to determine the electric field potential 454 at those discrete times. Selected electrodes of the lead are used as a sensor to make the measurements. The measurements represented by dots 456 follow the curve of the electric field potential 454 and will allow the construction of the electric field potential 454 by a processor or user. It will be understood that any sensor measurement constitutes a measurement made over a discrete period of time (for example, 0.1, 1, 10, 100, or more milliseconds or 1, 10, or 100, or more microseconds.) The discrete or intermittent sensor measurements sample the electric field potential in a non-continuous manner so that there is a period of time between each measurement period when the electric field potential is not being sampled or measured.

In at least some embodiments, discrete or intermittent sensor measurements can be advantageous over continuous sensor measuring or monitoring. For example, discrete or intermittent sensor measurements may save battery energy as compared to continuous monitoring due to the decreased measurement time. As another example, discrete or intermittent sensor measurements may reduce the amount of memory used for measurement storage as compared to continuous monitoring due to fewer datapoints being recorded and may also result in faster analysis or data transmission due to the accumulation of fewer datapoints for analysis (see, for example, step 606 of FIG. 6).

In at least some embodiments, the electric field potential can be interrogated using a therapeutic electrical stimulation pulse, as the electrical pulse 450. The therapeutic electrical stimulation pulse is often generated using a set of therapeutic stimulation parameters selected for the particular patient to provide the desired therapy. In at least some embodiments, the electric field potential can be interrogated using electrical pulses that are not intended to provide therapy. In at least some embodiments, the electric field potential can be interrogated using sub-perception electrical pulses. In some embodiments, any combination of therapeutic electrical stimulation pulses, non-therapeutic electrical pulses, or sub-perception electrical pulses can be used.

In some embodiments, the electrical pulses for interrogation utilize default values for the set of parameters used to generate the electrical pulses. Such parameters include any one or more of the following: amplitude, pulse width, pulse frequency, number of phases, polarity of each phase or pulse, or the like. The default values will provide the same electrical pulse for each patient which can simplify analysis (see, for example, step 606 of FIG. 6) of the measured electric field potentials when compared to embodiments in which the values of the parameters can be selected. In at least some of these embodiments, the system may allow user modification of the default values or selection of values other than the default values. In at least some embodiments, the parameters used for electrical pulses delivered for measurement are the same as the parameters used in electrical pulses delivered for therapy.

In other embodiments, pulses with different values for one or more of the parameters, such as different amplitudes, pulse widths, or combinations thereof, can be used. In some embodiments, a series of pulses with one or more varying parameters can be used to titrate or otherwise investigate the electric field potential under different interrogation conditions.

In at least some embodiments, the discrete or intermittent sensor measurements can include one, two, three, four, or more sensor measurements during each electrical pulse. In at least some embodiments, the discrete or intermittent sensor measurements can include one, two, three, four, or more sensor measurements during each phase of the electrical pulse.

In at least some embodiments, discrete or intermittent measurements can be performed periodically on a regular, irregular, random, or pseudo-random schedule. In at least some embodiments, the discrete or intermittent measurements can be performed periodically with a period in a range of 0.05 milliseconds to 1 second or longer, in a range of 0.1 millisecond to 0.1 second, in the range of 1 to 10 milliseconds, in the range of 1 millisecond to 1 second, in the range of 0.2 milliseconds to 1 millisecond, or in the range of 0.05 milliseconds to 0.2 milliseconds. For example, the period can be 0.1, 1, 10, or 100 milliseconds or 1 second or longer. Alternatively, the periodic discrete or intermittent measurements can be described as having a sampling rate in the range of 1 Hz to 20 kHz. in the range of 10 Hz to 10 kHz, in the range of 100 Hz to 1.2 kHz, in the range of 1 Hz to 1.2 kHz, in the range of 1 kHz to 5 kHz, or in the range of 5 kHz to 20 kHz. In other embodiments, the discrete or intermittent measurements can be performed with an average period in any of the ranges described above, but with random or pseudo-random variation (for example, ranging from ±5 to ±50% of the value of the period) in the period. In at least some embodiments, the period or sampling rate can be pre-set, user specified, or dynamically adjustable, or any combination thereof.

In some embodiments, the discrete or intermittent measurements can be made during the entire period of operation of the IPG or ETS. For example, measurements can commence and continue once the IPG or ETS is activated. As another example, the measurements can commence and continue during periods of time when the IPG or ETS is providing stimulation therapy.

In other embodiments, the discrete or intermittent measurements may be scheduled to only occur over a limited measurement period (for example, over 1, 5, 10, 20, or 30 minutes or 1, 2, or 4 hours or more) and then not performed for a measurement-off period (for example, 1, 5, 10, 20, or 30 minutes or 1, 2, or 4 hours or more). In at least some of these embodiments, a patient, clinician, or other user can schedule the measurement periods and measurement-off periods.

In other embodiments, the discrete or intermittent measurements may be scheduled to occur at regular intervals such as, for example, every 1, 2, 3, 4, 6, or 12 hours or every 5, 10, 15, or 30 minutes, or the like.

In yet other embodiments, the discrete or intermittent measurements may be scheduled to only occur for a limited number of electrical pulses and then not performed for a number of electrical pulses. For example, the discrete or intermittent measurements may be made during and after one electrical pulse and then not performed during the next electrical pulse and so on. As another example, the discrete or intermittent measurements may be made during and after two, three, four, five, or more electrical pulses and then not performed during the next two, three, four, five, or more electrical pulses and so on. The number of electrical pulses during which a measurement is made can be the same or different to the number of electrical pulses during which no measurement is made.

In some embodiments, the stimulation pulse phase may be used as gate signal to define the measurement time. For example, measurement can be turned on during the positive phase, or negative phase, or off phase, or during other phases of the stimulation pulse, or any combination thereof.

In some embodiments, the discrete or intermittent measurements may start or end as a result of a triggering event. Example of triggering events include, but are not limited to, the onset of stimulation, a switch to a new stimulation program, an adjustment of stimulation parameters, a user command (for example, a user issuing a command from a RC or CP to begin measurement), a detected change in patient posture or activity, a detected change in patient biological rhythm (for example, a change in heartbeat, heart rate, or respiration), or the like or any combination thereof. In at least some embodiments, the system may have measurement periods and measurement-off periods for sensor measurement, as described above, but also include sensor measurements in response to a triggering event that happens during a measurement-off period.

Figure 5A:
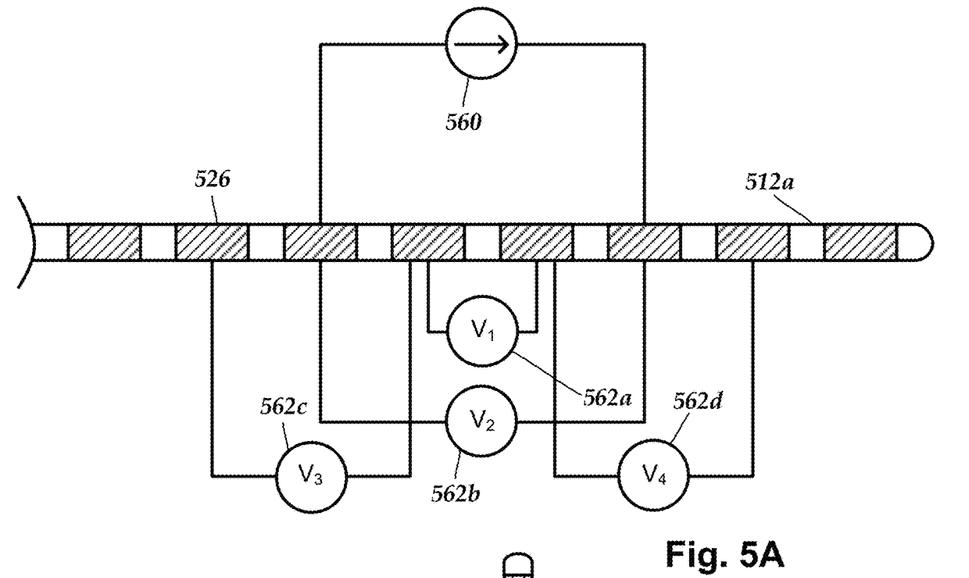
FIG. 5A is a schematic side view of one embodiment of a portion of a lead with electrodes that produce a single source configuration with four different sensor measurement configurations.

FIG. 5A illustrates one embodiment of a set of electrodes 526 of a lead 512a. In the illustrated embodiment, one or more electrical pulses are provided between electrodes 3 and 6, as indicated by source configuration 560. (The electrode numbers are counted from the proximal end of the electrode array.) Sensor measurements can then be made between any pair of electrodes. In the illustrated embodiments, the sensor measurement is a voltage measurement, but in other embodiments the sensor measurement can be a current measurement. Four possible sensor measurement configurations 562a, 562b, 562c, 562d are illustrated in FIG. 5A with sensor measurement configuration 562a between electrodes 4 and 5, sensor measurement configuration 562b between electrodes 3 and 6, sensor measurement configuration 562c between electrodes 2 and 4, and sensor measurement configuration 562d between electrodes 5 and 7. It will be recognized, however, that any other combination of electrodes can be used for a sensor measurement configuration. In addition, a sensor measurement configuration can be made between one of the electrodes 526 and an electrode 564 (FIG. 5B) that is not on the lead.

Figure 5B:
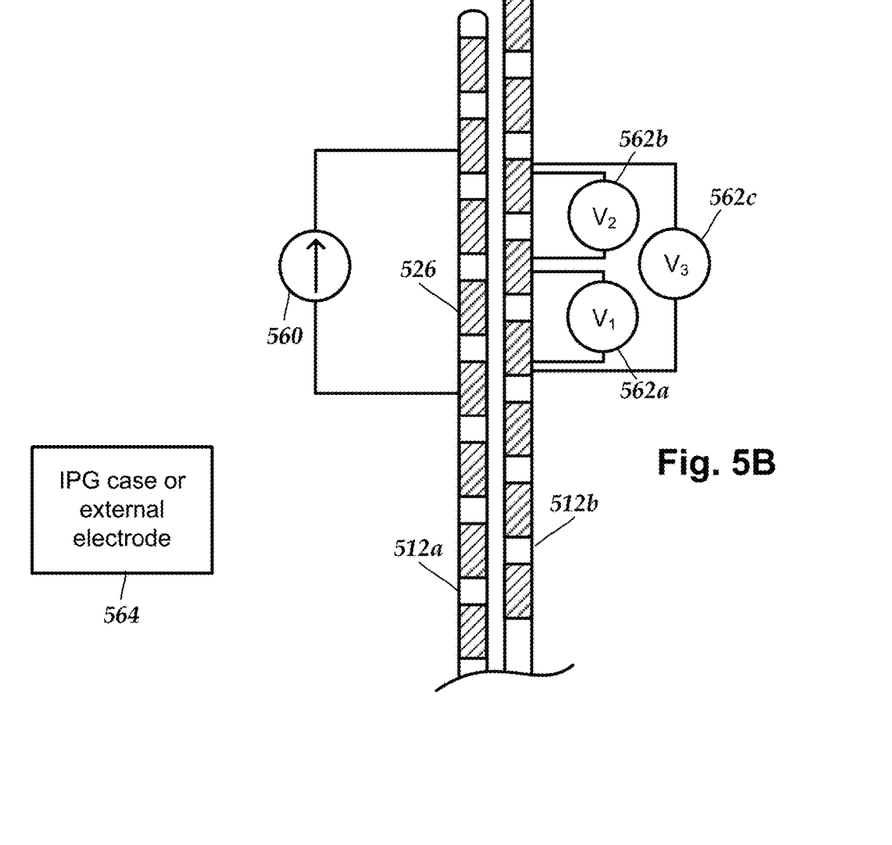
FIG. 5B is a schematic side view of one embodiment of a portion of two leads with electrodes that produce a single source configuration with three different sensor measurement configurations.

FIG. 5B illustrates one embodiment of two leads 512a, 512b which each have a set of electrodes 526. In the illustrated embodiment, one or more electrical pulses are provided between electrodes 4 and 7 of one lead 512a, as indicated by source configuration 560. Sensor measurements can then be made between any pair of electrodes on the other lead 512b. It will be recognized that any pair of electrodes on the first lead 512a can also be used to make sensor measurements. Three possible sensor measurement configurations 562a, 562b, 562c are illustrated in FIG. 5B with sensor measurement configuration 562a between electrodes 4 and 5 of lead 512b, sensor measurement configuration 562b between electrodes 5 and 6 of lead 512b, and sensor measurement configuration 562c between electrodes 4 and 6 of lead 512b. It will be recognized, however, that any other combination of electrodes can be used for a sensor measurement configuration. For example, sensor measurements can then be made between any pair of electrodes on the other lead 512b or between one electrode on lead 512a and another electrode on lead 512b. In addition, a sensor measurement can be made between one of the electrodes and an electrode 564 that is not on either of the leads. Such electrodes can be, for example, the case of the IPG acting as a second electrode or an external electrode (for example, a patch electrode) positioned on the body of the patient (for example, on the chest of the patient.) It will be recognized that, instead of two leads, a paddle lead or cuff lead with two or more columns of electrodes can be used.

In at least some embodiments, FIGS. 5A and 5B illustrate arrangements in which a single, fixed source configuration 560 of electrical pulses is used to interrogate the electric field potential and multiple pairs of electrodes are used for sensor measurement configurations 562a, 562b, 562c, 562d (FIG. 5A only).

Figure 5C:
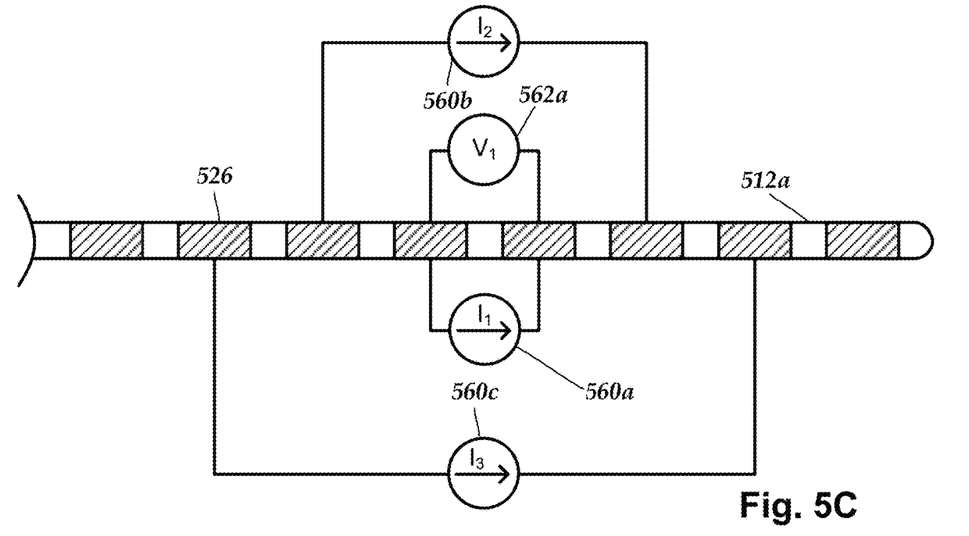
FIG. 5C is a schematic side view of one embodiment of a portion of a lead with electrodes that produce three source configurations with a single sensor measurement configuration.

FIG. 5C illustrates one embodiment of a set of electrodes 526 of a lead. In the illustrated embodiment, one or more electrical pulses are provided between either a) electrodes 4 and 5, as indicated by source configuration 560a, b) electrodes 3 and 6, as indicated by source configuration 560b, or c) electrodes 2 and 7, as indicated by source configuration 560c. It will be recognized, however, that any other combination of electrodes can be used for a source configuration. In addition, a source configuration can be made between one of the electrodes and an electrode 564 (FIG. 5D) that is not on the lead.

Sensor measurements can then be made between any pair of electrodes. One possible sensor measurement configurations 562a between electrodes 4 and 6 is illustrated in FIG. 5C. It will be recognized, however, that any other combination of electrodes can be used for a sensor measurement configuration. In addition, a sensor measurement can be made between one of the electrodes and an electrode 564 (FIG. 5D) that is not on the lead.

Figure 5D:
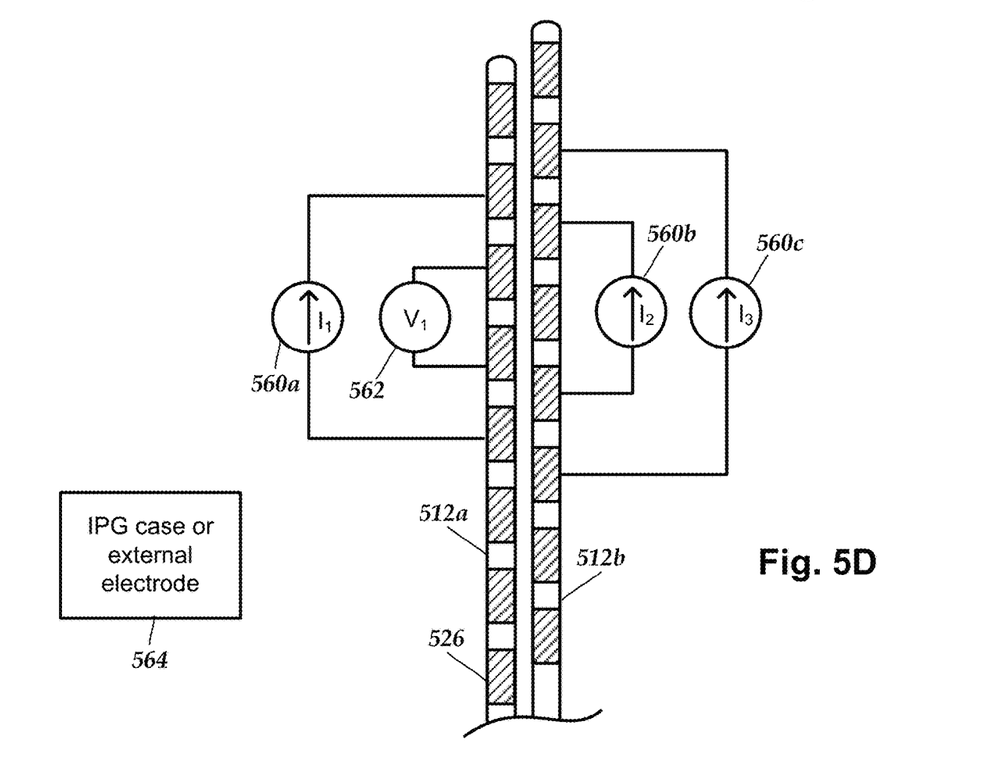
FIG. 5D is a schematic side view of one embodiment of a portion of two leads with electrodes that produce three source configurations with a single sensor measurement configuration.

FIG. 5D illustrates one embodiment of two leads 512a, 512b which each have a set of electrodes 526. In the illustrated embodiment, one or more electrical pulses are provided between either a) electrodes 4 and 7 of one lead 512a, as indicated by source configuration 560a, b) electrodes 4 and 6 of lead 512b, as indicated by source configuration 560b, or c) electrodes 3 and 7 of lead 512c, as indicated by source configuration 560c. Sensor measurements can then be made between any pair of electrodes on either lead 512a, 512b (for example, a pair of electrodes on the same lead or two electrodes on different leads). One possible sensor measurement configuration 562a between electrodes 5 and 6 of lead 512a is illustrated in FIG. 5D. It will be recognized, however, that any other combination of electrodes can be used for a sensor measurement configuration. In addition, a sensor measurement can be made between one of the electrodes and an electrode 564 that is not on either of the leads. Such electrodes can be, for example, the case of the IPG acting as a second electrode or an external electrode positioned on the body of the patient (for example, on the chest of the patient.) It will be recognized that, instead of two leads, a paddle lead or cuff lead with two or more columns of electrodes can be used.

In at least some embodiments, FIGS. 5C and 5D illustrate arrangements in which a single, fixed sensor measurement configuration 562a is used to measure the electric field potential that is interrogated using different source configurations 560a, 560b, 560c of electrical pulses. In at least some embodiments, the arrangements exemplified by the embodiments illustrated in FIGS. 5A to 5D can be combined to provide for multiple sensor measurement configurations to measure the electric field potential that is interrogated using multiple source configurations.

The examples in FIGS. 5A to 5D are illustrative examples of selection of source configurations and sensor measurement configurations. It will be recognized that other embodiments can include any number or type of leads, any number of source configurations, and any number of different sensor measurement configurations.

In some embodiments, the selection of electrodes and pulse parameters for the source configuration 560, 560a, 560b, 560c can correspond to, for example, the stimulation electrodes and parameters used to provide therapy and, therefore, can be different for each patient. These electrical pulses can be therapeutic stimulation pulses or can be non-therapeutic electrical pulses using pulse parameters selected for the patient.

In other embodiments, the selection of electrodes and pulse parameters for the source configuration 560, 560a, 560b, 560c (for making sensor measurements) can be the same for each patient. The electrical pulses may be non-therapeutic electrical pulses and may utilize default values for the parameters. These latter embodiments may result in sensor measurements that can be interpreted using a simpler analysis (see, for example, step 606 of FIG. 6) or algorithm because the electrode selection and pulse parameters are the same for each patient and electrical pulse. In contrast, the embodiments that utilize electrodes and parameters that can be selected and different for each patient (such as using therapeutic stimulation pulses) may require a more complex analysis (see, for example, step 606 of FIG. 6) or algorithm for interpreting the sensor measurements because the selection of electrodes and pulse parameters are variables.

With respect to the sensor measurements, the electrode pair selected for a sensor measurement configuration will typically result in measurement or observation of electric field potentials of the patient tissue between and near the two electrodes. Utilizing a single electrode on the lead and an electrode not on the lead (for example, the IPG case or an external electrode) will produce results that represent the tissue between the two electrodes. It will be recognized that one or more of the electrodes of the sensor measurement configuration can be a dedicated sensor electrode.

In at least some embodiments, all sensor measurements can be made using the same electrode pair. In other embodiments, sensor measurements may be made using two or more pairs of electrodes and may include simultaneous measurement with the two or more pairs, sequential measurement, or any other temporal arrangement of the measurements. In at least some embodiments, a differential between sensor measurements from two different pairs may be determined. The differential can remove or reduce common signals, such as artifacts, the pulses from the source configuration, and background, to enhance the signal-to-noise of the resulting measurements. In at least some embodiments, a normalized sensor measurements from two different pairs may be determined.

Figure 6:
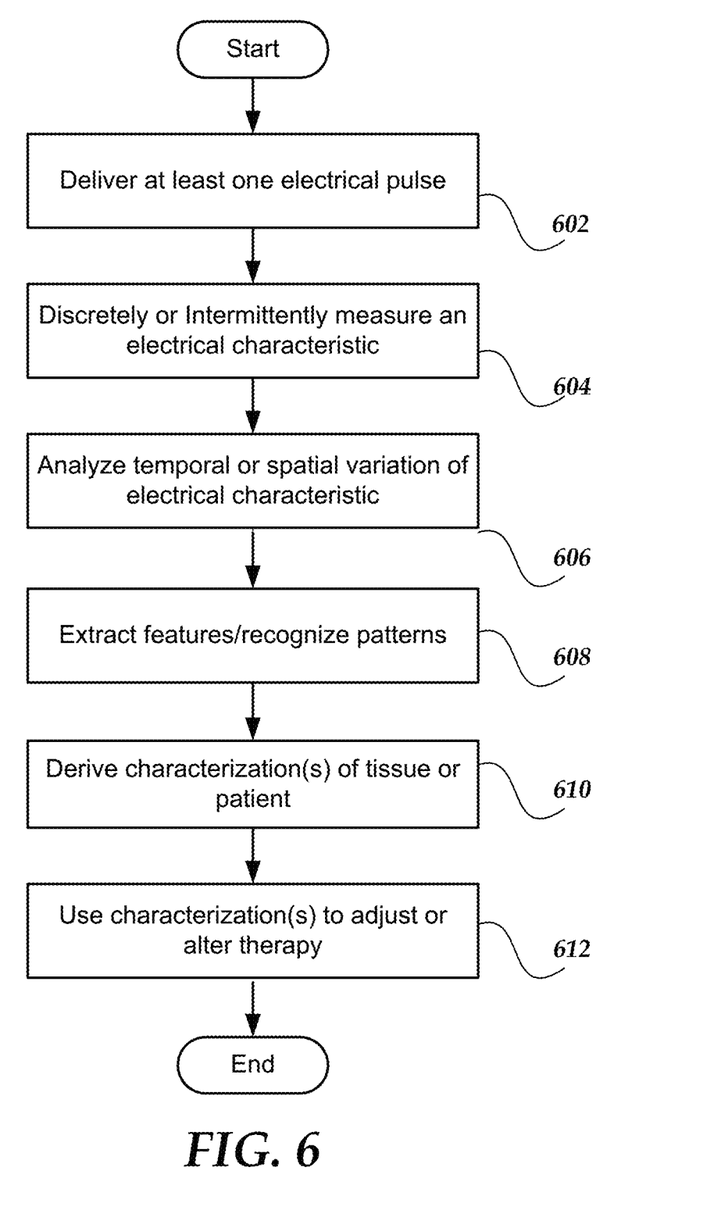
FIG. 6 is a flowchart of one embodiment of discretely measuring an electrical characteristic using electrodes on a lead.

FIG. 6 illustrates one embodiment of a method of measuring electrical characteristics using electrodes on one or more leads. In step 602, at least one electrical pulse is delivered using the electrodes of the lead(s). The electrical pulse can be a therapeutic stimulation pulse, a non-therapeutic electrical pulse, a sub-perception electrical pulse, or any other suitable pulse and can be monophasic, biphasic, or multiphasic and can be monopolar, bipolar, or multipolar. The electrical pulse may also be a train of pulses.

In step 604, an electrical characteristic, such as an electric field potential or local current, is discretely or intermittently measured during or after the delivery of the electrical pulse using at least one electrode of the lead(s). In many instances, the measurement will be made using two electrodes of the lead(s) or using multiple pairs of electrodes of the lead(s), but it will be understood that electrodes not on the lead can also be used.

In step 606, the sequence of discrete or intermittent measurements are then analyzed to produce information about the temporal or spatial variation in the electrical characteristic, such as the electric field potential or local current. The electric field potential may vary temporally due to stimulation and other electrical pulses, neural response, neural signals, heartbeat signals, respiration, patient activity (e.g., sleep, active, inactive, etc.), posture, and the like. In at least some embodiments, the measurements may be processed to compress or average the measurements and then can be stored locally or non-locally. In at least some embodiments, the measurements may be transmitted to a RC, CP, or other device for processing, pre-processing, storage, or the like.

In at least some embodiments, in step 608, the analysis of the sequence of discrete or intermittent measurements can be used to extract features or recognize patterns in the spatial or temporal variation of the electrical characteristic. The features or patterns can include, but are not limited to, the size and shape of peaks or valleys in the electrical characteristic, the frequency of positive or negative excursions, the rising and trailing slope of the signal change, or the like or any combination thereof. The features or patterns can also include those extracted from transformed data after pre-processing or transformation, for example, after applying Principal Component Analysis (PCA), Independent Component Analysis (ICA), linear regression (LR), or the like or any combination thereof.

In at least some embodiments, in step 610, these features or patterns can be used to derive characterization(s) of the tissue around the lead or the patient. For example, the features or patterns may be used to provide information about, for example, impedance, conductivity, or capacitance of the tissue near the lead or electrodes, stimulation induced voltage distribution, current intensity, or charging and discharging characteristics, changes associated with heart beat and respiration, changes associated with postural position or intensity of physical activities, as well as other electrical characteristics of the tissue, or the like or any combination thereof.

In at least some embodiments, in step 612, the characterizations(s) (or the features or patterns from step 608 or analysis from step 606) is used to alter or adjust the therapy. For example, stimulation parameters may be altered due to changes in patient posture or activity or due to migration of the lead which are indicated by the characterizations(s) of step 610 (or the features or patterns from step 608 or analysis from step 606).

Figure 7:
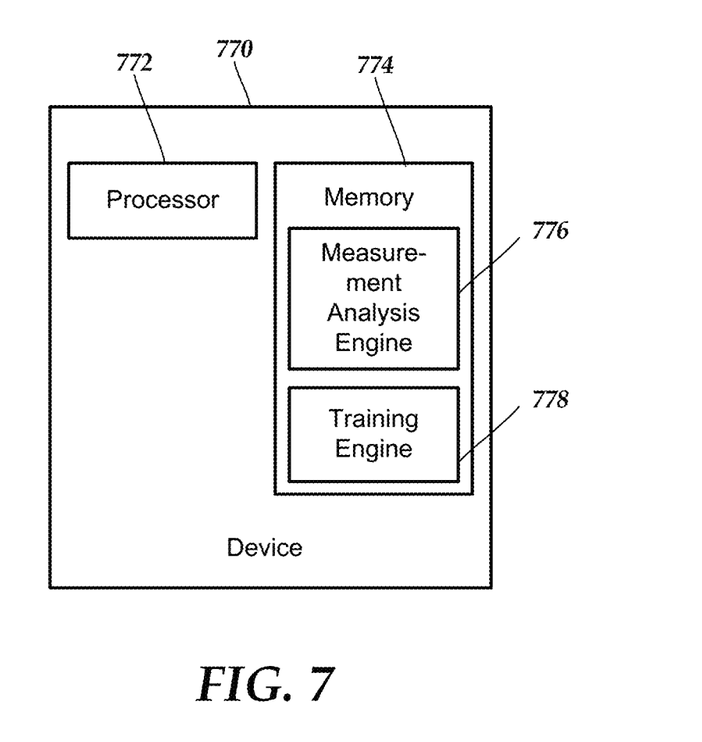
FIG. 7 is a schematic block diagram of a device with a processor and memory and a measurement analysis engine and optional training engine stored in the memory.

In at least some embodiments, steps 606 to 612 (or any subset of these steps) can be performed by a measurement analysis engine 776 (or a measurement analysis module or measurement analysis algorithm) residing in a memory 774 and operating in a processor 772 of a device 770 as illustrated in FIG. 7. The device 770 can be, for example, devices illustrated in FIG. 1, such as an IPG 14, RC 16, CP 18, or ETS 20, or any other suitable device, including mobile devices. In some embodiments, the processor 772, or portions of the processing, are non-local to the device, such as cloud-based processing.

The measurement analysis engine 776 can be configured to perform the analysis based on training of the measurement analysis engine 776 using a set of training measurements. Machine learning and artificial intelligence techniques for modifying and refining an algorithm using a set of training input, such as the training measurements, are known. Any suitable machine learning or artificial intelligence techniques, or combination of techniques, can be used to train the measurement analysis engine. Examples of machine learning and artificial intelligence techniques include, but are not limited to, supervised and unsupervised machine learning and artificial intelligence techniques, such as, for example, Bayesian networks, support vector machines (SVMs), neural networks, genetic algorithms, or the like. These techniques may utilize classification, regression, backpropagation, or the like.

The training can include making measurements in a training environment. The training measurements are independently identified as including specific features, patterns, tissue characteristics, or patient characteristics. The measurement analysis engine analyzes the training measurements and then compares the result to the independent identifications. These comparisons can be used to refine the measurement analysis engine to improve the accuracy of the results. The comparisons may be used to refine the source or measurement configurations. For example, configurations that are not sensitive may be trimmed and configurations with substantial sensitivity may be reinforced.

In some embodiments, the IPG 14, RC 16, CP 18, or ETS 20 may include a training engine 778 that permits training the measurement analysis engine 776 in a training session using lead(s) implanted in the patient with identifications of specific features, patterns, tissue characteristics, or patient characteristics provided by the patient, clinician, or other user. Such a training session can include performing the method of FIG. 6 with the additional steps of 1) inputting an identification of specific features, patterns, tissue characteristics, or patient characteristics that occurred during the discrete or intermittent measuring; 2) comparing the input identifications with the results of steps 606 to 610; and 3) refining the measurement analysis engine using the comparisons. In some embodiments, the patient may be instructed to perform particular activities or to assume particular postures.

The training engine 778 may also be useful outside of a specific training session. For example, the patient may be queried by the RC 16 regarding a current or past activity or posture of the patient and the results of the query may be combined with the discrete or intermittent measurements associated with the time period to train the measurement analysis engine.

In at least some embodiments, refinements to the measurement analysis engine 776 may be uploaded to a database or server and used to further refine a master measurement analysis engine. In at least some embodiments, refinements to the measurement analysis engine may be downloaded to the device 770 to modify or replace the measurement analysis engine 776 stored in the memory 774.

It will be understood that each block of the flowchart illustration, and combinations of blocks in the flowchart illustration and methods disclosed herein, can be implemented by computer program instructions. These program instructions may be provided to a processor to produce a machine, such that the instructions, which execute on the processor, create means for implementing the actions specified in the flowchart block or blocks disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computing device. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device. The computer program instructions can be stored locally or nonlocally (for example, in the Cloud).

Figure 8:
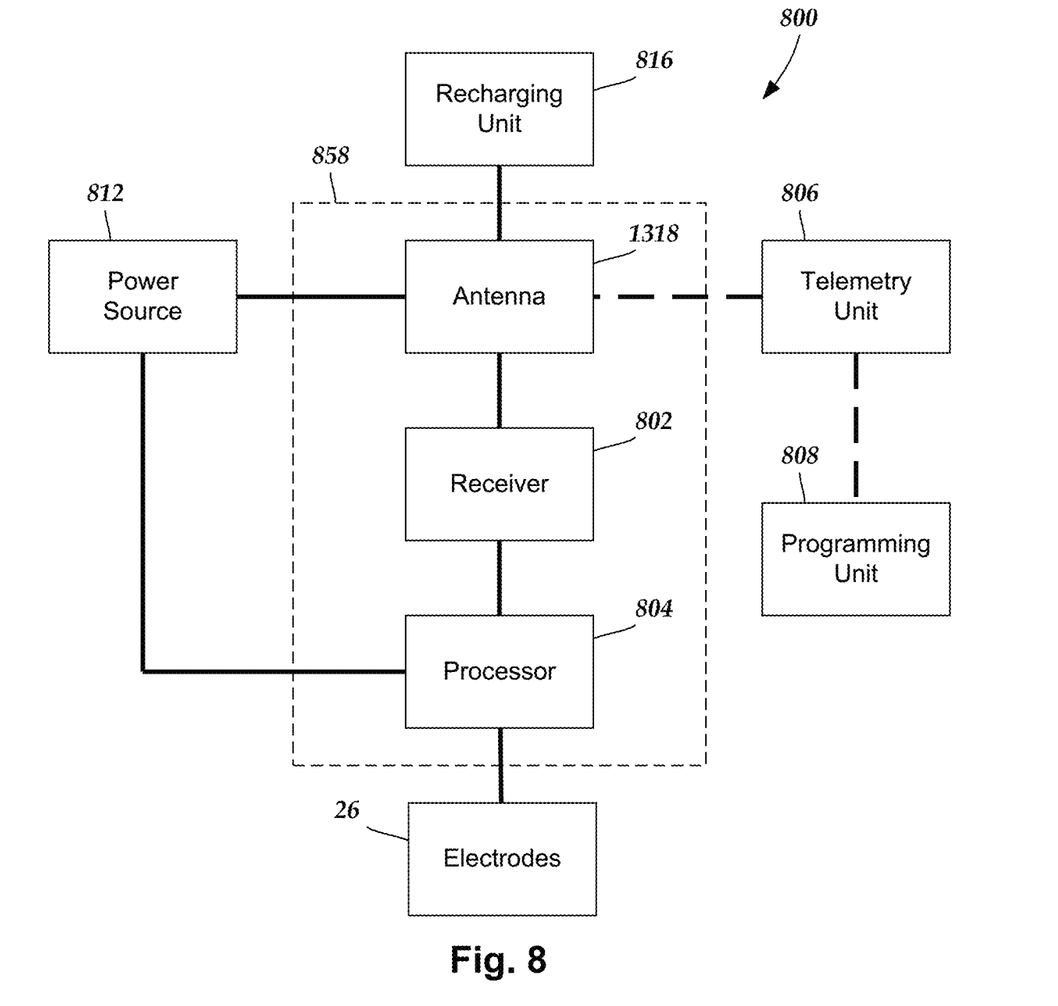
FIG. 8 is a schematic overview of one embodiment of components of a stimulation system, including an electronic subassembly disposed within a control module such as an IPG or ETS.

FIG. 8 is a schematic overview of one embodiment of components of an electrical stimulation system 800 including an electronic subassembly 858 disposed within a control module. The electronic subassembly 858 may include one or more components of the IPG. It will be understood that the electrical stimulation system can include more, fewer, or different components and can have a variety of different configurations including those configurations disclosed in the stimulator references cited herein.

Some of the components (for example, a power source 812, an antenna 818, a receiver 802, and a processor 804) of the electrical stimulation system can be positioned on one or more circuit boards or similar carriers within a sealed housing of an implantable pulse generator (see e.g., 14 in FIG. 1), if desired. Any power source 812 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bio-energy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 818 or a secondary antenna. In at least some embodiments, the antenna 818 (or the secondary antenna) is implemented using the auxiliary electrically-conductive conductor. The external power source can be in a device that is mounted on the skin of the user or in a unit that is provided near the user on a permanent or periodic basis.

If the power source 812 is a rechargeable battery, the battery may be recharged using the optional antenna 818, if desired. Power can be provided to the battery for recharging by inductively coupling the battery through the antenna to a recharging unit 816 external to the user. Examples of such arrangements can be found in the references identified above. The electronic subassembly 858 and, optionally, the power source 812 can be disposed within a control module (e.g., the IPG 14 or the ETS 20 of FIG. 1).

In one embodiment, electrical stimulation signals are emitted by the electrodes 26 to stimulate nerve fibers, muscle fibers, or other body tissues near the electrical stimulation system. The processor 804 is generally included to control the timing and electrical characteristics of the electrical stimulation system. For example, the processor 804 can, if desired, control one or more of the timing, frequency, strength, duration, and waveform of the pulses. In addition, the processor 804 can select which electrodes can be used to provide stimulation, if desired. In some embodiments, the processor 804 selects which electrode(s) are cathodes and which electrode(s) are anodes. In some embodiments, the processor 804 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 808 that, for example, allows modification of pulse characteristics. In the illustrated embodiment, the processor 804 is coupled to a receiver 802 which, in turn, is coupled to the optional antenna 818. This allows the processor 804 to receive instructions from an external source to, for example, direct the pulse characteristics and the selection of electrodes, if desired.

In one embodiment, the antenna 818 is capable of receiving signals (e.g., RF signals) from an external telemetry unit 806 which is programmed by the programming unit 808. The programming unit 808 can be external to, or part of, the telemetry unit 806. The telemetry unit 806 can be a device that is worn on the skin of the user or can be carried by the user and can have a form similar to a pager, cellular phone, or remote control, if desired. As another alternative, the telemetry unit 806 may not be worn or carried by the user but may only be available at a home station or at a clinician's office. The programming unit 808 can be any unit that can provide information to the telemetry unit 806 for transmission to the electrical stimulation system 800. The programming unit 808 can be part of the telemetry unit 806 or can provide signals or information to the telemetry unit 806 via a wireless or wired connection. One example of a suitable programming unit is a computer operated by the user or clinician to send signals to the telemetry unit 806.

The signals sent to the processor 804 via the antenna 818 and the receiver 1302 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 800 to cease operation, to start operation, to start charging the battery, or to stop charging the battery. In other embodiments, the stimulation system does not include the antenna 818 or receiver 802 and the processor 804 operates as programmed.

Optionally, the electrical stimulation system 800 may include a transmitter (not shown) coupled to the processor 804 and the antenna 818 for transmitting signals back to the telemetry unit 806 or another unit capable of receiving the signals. For example, the electrical stimulation system 800 may transmit signals indicating whether the electrical stimulation system 800 is operating properly or not or indicating when the battery needs to be charged or the level of charge remaining in the battery. The processor 804 may also be capable of transmitting information about the pulse characteristics so that a user or clinician can determine or verify the characteristics.

The above specification and examples provide a description of the manufacture and use of the invention. Since many embodiments of the invention can be made without depart-

What is claimed as new and desired to be protected by Letters Patent of the United States is:

1. An electrical stimulation system, comprising:
   at least one electrical stimulation lead, each of the at least one electrical stimulation lead comprising a plurality of stimulation electrodes; and
   a processor coupled to the at least one electrical stimulation lead and configured to perform actions, comprising:
      directing delivery of an electrical pulse through at least one of the stimulation electrodes of the at least one electrical stimulation lead to tissue of a patient; and
      directing discrete measurement of an electrical characteristic of the tissue using at least one of the stimulation electrodes of the at least one electrical stimulation lead during, and after, delivery of the electrical pulse to the tissue of the patient.

2. The electrical stimulation system of claim 1, wherein the electrical characteristic is an electric field potential.

3. The electrical stimulation system of claim 1, wherein the electrical pulse is a therapeutic stimulation pulse.

4. The electrical stimulation system of claim 1, wherein the electrical pulse is not a therapeutic stimulation pulse.

5. The electrical stimulation system of claim 1, wherein the electrical pulse has an intensity that is at a sub-perception level.

6. The electrical stimulation system of claim 1, wherein directing delivery comprises directing delivery of the electrical pulse through two of the stimulation electrodes.

7. The electrical stimulation system of claim 1, wherein directing delivery comprises directing delivery of the electrical pulse through a first pair of the stimulation electrodes, the actions further comprising directing delivery of a second electrical pulse through a second pair of the stimulation electrodes.

8. The electrical stimulation system of claim 7, wherein directing discrete measurement comprises directing discrete measurement of the electrical characteristic of the tissue using a first pair of the stimulation electrodes to produce a set of first measurements and directing discrete measurement of the electrical characteristic of the tissue using a second pair of the stimulation electrodes to produce a set of second measurements.

9. The electrical stimulation system of claim 8, wherein directing discrete measurement comprises producing the first measurements and the second measurements during, and after, both the electrical pulse and the second electrical pulse.

10. The electrical stimulation system of claim 1, wherein directing discrete measurement comprises directing discrete measurement of the electrical characteristic of the tissue using two of the stimulation electrodes.

11. The electrical stimulation system of claim 1, wherein directing discrete measurement comprises directing discrete measurement of the electrical characteristic of the tissue using a first pair of the stimulation electrodes to produce a set of first measurements and directing discrete measurement of the electrical characteristic of the tissue using a second pair of the stimulation electrodes to produce a set of second measurements.

12. The electrical stimulation system of claim 11, wherein the actions further comprise determining a differential measurement by subtracting one of the first measurements from one of the second measurements.

13. The electrical stimulation system of claim 1, wherein the actions further comprise analyzing the discrete measurements to identify a temporal or spatial variation of the electrical characteristic.

14. The electrical stimulation system of claim 13, wherein the actions further comprise extracting a feature or recognizing a pattern in the discrete measurements or the temporal or spatial variation of the electrical characteristic.

15. The electrical stimulation system of claim 14, wherein the actions further comprise deriving a characterization of the tissue or the patient using the extracted feature or the recognized pattern in the discrete measurements or the temporal or spatial variation of the electrical characteristic.

16. The electrical stimulation system of claim 15, wherein the actions further comprise altering a set of stimulation parameters based on the characterization of the tissue or the patient, the extracted feature, or the recognized pattern in the discrete measurements or the temporal or spatial variation of the electrical characteristic.

17. The electrical stimulation system of claim 1, wherein the electrical pulse comprises at least two phases and directing discrete measurement comprises directing at least one measurement during each of the at least two phases of the electrical pulse.

18. The electrical stimulation system of claim 1, wherein directing discrete measurement comprises directing discrete measurement to start or end only after occurrence of a triggering event.

19. The electrical stimulation system of claim 1, wherein directing discrete measurement comprises directing discrete measurement only during scheduled measurement periods with no measurement occurring during scheduled measurement-off periods.

20. A non-transitory computer-readable medium having stored thereon instructions for execution by a processor, including:
   directing delivery of an electrical pulse through at least one stimulation electrode of at least one electrical stimulation lead to tissue of a patient; and
   directing discrete measurement of an electrical characteristic of the tissue using at least one stimulation electrode of the at least one electrical stimulation lead during, and after, delivery of the electrical pulse to the tissue of the patient.

* * * * *